United States Patent
Smith et al.

[19]

[11] Patent Number: 5,880,504
[45] Date of Patent: Mar. 9, 1999

[54] EXAMINING A DIAMOND

[75] Inventors: Martin Phillip Smith, Wargrave; James Gordon Charters Smith, High Wycombe; Martin Cooper, Marlow; Christopher Mark Welbourn, Waltham St Lawrence; Philip Maurice Martineau, Bourne End, all of United Kingdom

[73] Assignee: Gersan Establishment, Liechtenstein

[21] Appl. No.: 809,152

[22] PCT Filed: Sep. 5, 1995

[86] PCT No.: PCT/GB95/02093

§ 371 Date: Jul. 21, 1997

§ 102(e) Date: Jul. 21, 1997

[87] PCT Pub. No.: WO96/07896

PCT Pub. Date: Mar. 14, 1996

[30] Foreign Application Priority Data

Sep. 7, 1994 [GB] United Kingdom .................. 9418049

[51] Int. Cl.⁶ ..................................................... G01N 21/87
[52] U.S. Cl. ............................................. 250/372; 356/30
[58] Field of Search ................................ 250/372; 356/30

[56] References Cited

U.S. PATENT DOCUMENTS 5,164,586   11/1992   Hohberg et al. ..................... 250/226
5,536,943   7/1996    Smith et al. ........................ 250/372

FOREIGN PATENT DOCUMENTS

| 2 528 580 (A1) | 12/1983 | France | 356/30 |
| 32 36 817 (A1) | 4/1984 | Germany | 356/30 |
| 2 110 416 | 6/1983 | United Kingdom | 356/30 |

*Primary Examiner*—Constantine Hannaher
*Attorney, Agent, or Firm*—Cesari and McKenna, LLP

[57] ABSTRACT

In order to test whether a diamond has had a layer of synthetic diamond deposited thereon, the surface area of the natural part of the stone is measured by measuring the radiant-flux density of radiation substantially of wavelength 230 nm to 320 nm in an integrating sphere containing the diamond. This is compared to the total surface area of the diamond.

5 Claims, 1 Drawing Sheet

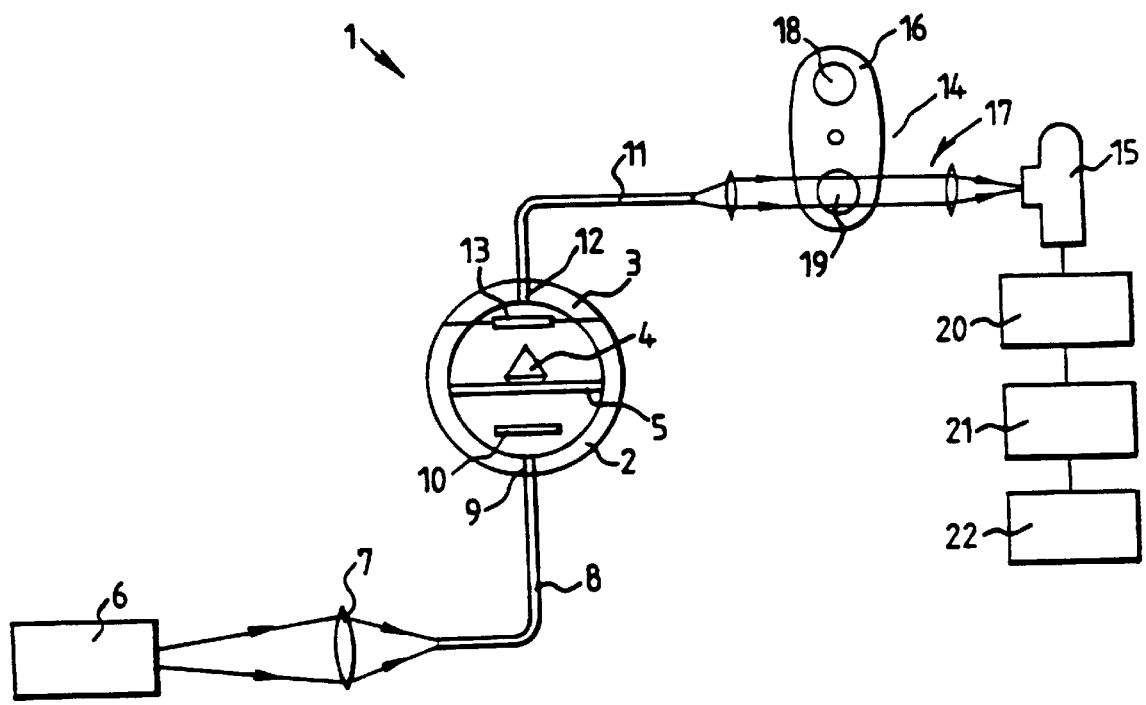

EXAMINING A DIAMOND

BACKGROUND TO THE INVENTION

The present invention relates to a method of and apparatus for examining a diamond. For example, the invention may be used to test whether a diamond has had a layer of synthetic diamond deposited thereon. This is of particular importance in detecting whether the diamond comprises CVD diamond material and also in locating such material if present.

Over the years, a number of methods of synthesising diamond material have been developed. One of these methods is the chemical vapor deposition (CVD) technique, which is a low pressure technique involving deposition of synthetic diamond (referred to as CVD diamond material in this specification) onto a substrate from a gas.

The synthetic diamond material may be deposited on an uncut or part-worked natural diamond which is then worked, for example, into a round brilliant cut. Alternatively, the synthetic diamond coating may be deposited onto a fully fashioned brilliant stone after working of the stone. The thickness of such a synthetic diamond material layer may be very thin—it could be in the range from 1 μm to 0.1 mm.

The value of a diamond is in part dependent upon its weight. Accordingly, synthetic diamond material such as CVD diamond material may be deposited onto natural gem diamonds, before or after cutting of the diamond, to increase the weight of the finished product. A diamond artificially enlarged by deposition of CVD diamond material is referred to in this specification as a "CVD/natural diamond doublet".

However, the value of a diamond also resides in its qualities of authenticity and uniqueness and in the fact that it is an entirely natural product. Thus, a diamond that has not been enlarged by deposition of synthetic diamond material has a value over a CVD/natural diamond doublet.

CVD diamond material may be deposited on a non-diamond or diamond substrate. In the latter case, the CVD diamond material can replicate the structure of the diamond substrate (referred to "homoepitaxial growth"). The CVD/natural diamond doublet produced can be identical in appearance, density and other common physical properties to an entirely natural diamond and there may be a problem in identifying such a CVD/natural diamond doublet.

It is an object of the present invention to provide a method of and apparatus for testing whether a diamond has had a layer of synthetic diamond deposited thereon.

It is desired that the apparatus should be simple and inexpensive and may be put into operation by a person with relatively little training. The method and apparatus should be capable of being operated reliably and consistently by a practised jeweller who has no training in laboratory gemological analysis.

THE INVENTION

The present invention provides a method of and apparatus for testing whether a diamond has had a layer of synthetic diamond deposited thereon, as set forth in claim 1 or 3. Preferred and/or optional features of the invention are set forth in claims 2 and 5.

The present inventors have discovered that if there is a difference between the surface area of the region of a diamond that strongly absorbs radiation substantially of wavelength substantially in the range 230 nm to 320 nm and the total surface area, a synthetic layer is present. Such radiation is substantially unabsorbed by the synthetic part and penetrates through it to the underlying natural material, where it will normally be absorbed. Synthetic diamond material, if present, will normally be deposited onto an area of a diamond and, unless that area is a re-entrant in the surface of the diamond, will tend to increase the surface area of the diamond. As the layer may be very thin (depth of the order of microns) the net increase in surface area may be very small, but is nevertheless detectable with sufficiently sensitive equipment.

An integrating enclosure provides a particularly effective way of measuring the surface area of the region of the diamond strongly absorbing the radiation of interest. The interior of the integrating enclosure is irradiated such that the irradiating radiation strikes the surface of the enclosure before striking the diamond, the flux of the radiation of interest in the integrating enclosure being sensed to give a signal dependent upon the surface area of the region of the diamond that strongly absorbs such radiation. Any suitable radiation sensor or detector may be used, such as a photo-multiplier tube or any similar known device.

Suitably, the integrating enclosure comprises an integrating sphere 35 mm in diameter. The integrating enclosure may be lined with SPECTRALON ®, which is a highly lambertain thermoplastic resin, and has a high reflectivity in the ultraviolet part of the spectrum.

It may be arranged that the irradiating radiation strikes the walls of the integrating enclosure before striking the diamond by directing the irradiating radiation onto the walls or onto baffles which reflect the radiation onto the walls or by any other suitable means. The diamond is thus irradiated diffusely with ultraviolet light.

A shelf which is substantially ultraviolet transparent may be provided in the enclosure so that the diamond may be supported in the enclosure, for example substantially centrally. A suitable ultraviolet transparent material is fused silica.

Ultraviolet light, generated for example by a xenon or deuterium lamp or any other suitable known source of ultraviolet radiation, may be fed to the diamond, for example by a fiber optic.

Means for detecting the radiant-flux density in the enclosure may comprise a fiber optic whose tip projects into the enclosure. An ultraviolet reflective baffle may be provided facing the tip of the fiber optic. The intensity of radiation passing down the fiber optic may be sensed by a detector such as a photomultiplier tube to give a signal dependent upon the radiant-flux density.

Filter means passing radiation of wavelength substantially in the range 230 nm to 320 nm may be provided between the means for detecting the radiant-flux density and the integrating enclosure. The area that strongly absorbs radiation at the wavelength of interest may be computed by any suitable known computing means suitably programmed, or any suitable electronic circuitry or by any suitable known meter or other similar means for giving a readable indication of the intensity of radiation transmitted, to allow the operator to calculate the surface area accordingly.

A signal dependent upon the surface area of the region of the diamond which strongly absorbs the radiation of interest may be provided by first finding the ratio R of the radiant-flux density in the enclosure when the diamond is in it to the radiant-flux density when there is no diamond in the integrating enclosure. The quantity S is then calculated as follows:

$$S = \left( \frac{1}{R} - 1 \right)$$

The quantity S is proportional to the surface area of the absorbing material of the diamond. This quantity can be compared to a quantity representative of the total surface area of the diamond.

The total surface area of the diamond may be measured, calculated or known from earlier studies. Preferably, the total surface area of the diamond is measured by measuring the surface area of the diamond which strongly absorbs radiation of a wavelength which is known to be strongly absorbed by all types of diamond. Any suitable known means for calculating the total surface area of the diamond may be used, including the apparatus for calculating the area that strongly absorbs radiation at the first-mentioned wavelength. Preferably, the integrating enclosure is irradiated with such radiation and the value S' calculated as in the following equation:

$$S' = \left( \frac{1}{R'} - 1 \right)$$

where R' is the ratio of the radiant-flux density of such radiation in the enclosure when the diamond is in the integrating enclosure to the radiant-flux density when there is no diamond in the integrating enclosure.

The values of S and S' may be then compared. The presence of a layer of synthetic diamond may be deduced if the first area (and hence S) is 99.8% or 99.9% or less of the total surface area, represented by S'.

For example, the radiant-flux density of radiation substantially of wavelength less than about 230 nm preferably less than 225 nm (far ultraviolet) may be measured. Preferably, the same integrating enclosure and radiation source is used as for the measurements of the first mentioned radiation. In this case, a filter passing radiation of wavelength less than about 230 nm may be provided between the source and the integrating enclosure and/or the detecting means for detecting the flux density.

Preferably therefore, the filter comprises means for mounting a filter passing radiation of wavelength less than about 230 nm and a filter passing radiation of wavelength substantially in the range 230 nm to 320 nm, the filter means allowing whichever filter is required to be placed between the integrating enclosure and the source and/or the detecting means. The mounting means may be any suitable structure in which filters can be mounted. For example, a filter wheel may be used.

It is also possible to use a wavelength of around 5,000 nm (in the infrared). However, a separate integrating enclosure with a gold lining would have to be provided for use with infrared radiation, because the reflectivity of SPECTRALON ® in the infrared is poor.

The irradiating radiation must contain some radiation of wavelength falling in the range substantially 230 nm to 320 nm. Radiation of wavelength outside this range may accompany the irradiating radiation. Preferably, however, a filter passing radiation substantially in the range 230 nm to 320 nm is provided between the diamond and the detecting means.

A filter passing radiation of wavelength substantially in the range 230 nm to 320 nm may be provided between the source of radiation and the diamond. If so, it is again preferable to provide a filter between the diamond and the detector in order to prevent the intensity of radiation generated by fluorescence being observed, as this could also give incorrect results.

Similarly, where radiation of wavelength less than about 230 nm is used to measure the total surface area of the diamond, the diamond may be irradiated with radiation of higher wavelengths, but it should be ensured that radiation substantially of wavelength less than about 230 nm is observed.

It will be tolerable to observe some radiation which is not of wavelength substantially in the range 230 nm to 320 nm, as long as the ratio of the intensity of such radiation to the intensity of radiation falling within the desired range is not substantial enough to make the observations uninterpretable by swamping out the contribution to the observed signal from the desired range. Similarly, it will be tolerable to observe some radiation of wavelength greater than 230 nm, as long as the ratio of the intensity of such radiation to the intensity of radiation of wavelength less than 230 nm is not too great.

It is preferred to calibrate the integrating enclosure to allow for variation in reflectivity of the enclosure with wavelength. This may be achieved by using a standard diamond of known quality and measuring the radiant-flux density in the enclosure at known wavelengths with the diamond of known quality.

The invention is particularly suitable for automation. For example, a feeder may be provided for feeding the diamond into and out of the integrating enclosure. For example, the diamond may be fed through the integrating enclosure in free flight, means being provided to sense when the diamond is in the enclosure.

Where fiber optics are used, they are preferably of fused silica, as this transmits high energy UV radiation well.

Alternatively, the diamond may be fed into and out of the enclosure by hand, the required measurements of the radiant-flux density in the enclosure being carried out automatically by the machine. A processor may be provided to calculate the values S and S' automatically, to compare them and to output a signal indicating that the diamond is a CVD/natural diamond doublet if the difference or ratio of the values S and S' is above a preset value. Such apparatus may be operated by unskilled operators with little previous training.

The invention will be further described by way of example only with reference to the accompanying drawings, in which:

BRIEF DESCRIPTION OF THE DRAWING

The FIGURE is a schematic illustration of apparatus according to the invention for examining a diamond.

PREFERRED EMBODIMENT

The apparatus 1 comprises an integrating sphere 2 which is lined with SPECTRALON ®. The top part 3 of the sphere is made detatchable to permit a diamond 4 to be placed in the sphere 2.

When in the sphere, the diamond is mounted on a shelf 5 made of fused silica, which is substantially transparent to high energy ultra violet radiation.

The interior of the sphere 5 is irradiated with ultraviolet radiation comprising radiation falling in the range 230 nm to 320 nm by a system comprising a UV source 6, in this case a xenon flash lamp, an optical system 7 (comprising fused silica optical elements) and a fused silica fiber optic 8. The end 9 of the fiber optic 8 projects into the sphere and is located opposite an ultraviolet reflective baffle 10, which ensures that the irradiating radiation strikes the walls of the sphere 2 before striking the diamond 4.

The radiant-flux density in the sphere 5 is measured by a system comprising a further fiber optic 11 whose tip 12 extends into the sphere opposite a UV reflective baffle 13, an optical system 14 and a photomultiplier tube 15.

The optical system 14 comprises a filter wheel and a fused silica lens system 17, for directing radiation through filters 18 and 19 in the filter wheel 16 and onto the photomultiplier tube 15.

The filter wheel 14 may be rotated so that filter 18 or 19 intersects the radiation. Filter 18 comprises a dielectric filter transmitting radiation of wavelength falling substantially in the range 230 nm to 290 nm. Filter 19 comprises a dielectric filter transmitting radiation of wavelength less than 225 nm. The signal from photomultiplier tube 15 is passed to an amplifier 20, whose output is connected to an analog/digital converter 21. The output of the converter 21 is connected to a processor 22.

The apparatus shown in the Figure is used as follows.

First, the sphere is irradiatied with no diamond in the sphere using source 6. The signal output by photomultiplier tube 15 at the wavelength passed by each of filters 18 and 19 is then measured, to provide a signal proportional to the radiant-flux density in the sphere 2 at those wavelengths, and stored in processor 22.

Next a diamond 4 is placed on the shelf 5 in the sphere 2. The sphere is then illuminated using source 6, and the signal output by photomultiplier tube 15 for each of the wavelengths passed by the filters 18 and 19 is measured, to provide a signal dependent upon the radiant-flux density in the sphere 2 for each of those wavelengths. These signals are stored in microprocessor 22.

The signals stored in the processor 22 are then manipulated as follows. The ratio R between the signal representative of the radiant-flux density at the wavelength passed by the filter 18 when the stone is in the sphere to the signal representative of the radiant-flux density in the sphere when there is no stone in the sphere is calculated. The value R', being the corresponding ratio for the wavelength passed by filter 19, is then calculated. Next, the quantities S and S' are calculated as set out above.

Then the difference or ratio of the signals S and S' is calculated. If this ratio is lower than a preset figure (for example 0.999 or 0.998), the processor 22 outputs a signal indicating that the stone probably comprises a natural stone with a CVD diamond layer on it.

The present invention has been described above purely by way of example, and modifications can be made within the invention. The invention also consists in any individual features described or implicit herein or shown or implicit in the drawings or any combination of such features or any generalization of any such features or combination.

We claim:

1. A method of testing whether a diamond has had a layer of synthetic diamond deposited thereon, comprising:
   placing the diamond in an integrating enclosure;
   irradiating the interior of the integrating enclosure with radiation including radiation of wavelength substantially in the range 230 nm to 320 nm such that the radiation strikes the surface of the integrating enclosure before striking the diamond;
   sensing the flux of the radiation substantially of wavelength substantially in the range 230 nm to 320 nm in the integrating enclosure, to give a first signal representative of the flux of radiation substantially of wavelength substantially in the range 230 nm to 320 nm in the integrating enclosure when the diamond is in the integrating enclosure;
   combining said first signal with a second signal dependent upon the flux of the said radiation in the integrating enclosure when no diamond is in the integrating enclosure, to give a signal dependent upon the surface area of the region of the diamond that strongly absorbs the first mentioned radiation;
   irradiating the interior of the integrating enclosure with further radiation, which is substantially of wavelength less than about 230 nm;
   combining a signal dependent upon the flux of the further radiation in the integrating enclosure when the diamond is in the integrating enclosure with a signal dependent upon the flux of the further radiation in the integrating enclosure when no diamond is in the integrating enclosure to give a signal dependent upon the total surface area of the diamond;
   comparing the surface area of the region of the diamond that strongly absorbs the first mentioned radiation with the total surface area of the diamond; and
   deducing the presence of a layer of synthetic diamond if the first mentioned area is different to the total surface area.

2. The method of claim 1, when carried out automatically.

3. Apparatus for testing whether a diamond has had a layer of synthetic diamond deposited thereon, comprising:
   an integrating enclosure, for enclosing the diamond;
   means for irradiating the interior of the integrating enclosure with ultra-violet radiation such that the radiation strikes a surface of the integrating enclosure before striking the diamond;
   means for sensing the flux of radiation substantially of wavelength substantially in the range 230 nm to 320 nm in the integrating enclosure and giving a first signal representative of the flux of radiation substantially in the range 230 nm to 320 nm in the integrating enclosure when the diamond is in the integrating enclosure, and a second signal representative of the flux of the said radiation in the integrating enclosure when no diamond is in the integrating enclosure;
   means for combining said first and second signals to give a signal dependent upon the surface area of the region of the diamond that strongly absorbs the first-mentioned radiation;
   means for sensing the flux of radiation of wavelength less than about 230 nm in the integrating enclosure and giving a third signal representative of the flux of radiation of wavelength less than about 230 nm in the integrating enclosure when the diamond is in the integrating enclosure, and a fourth signal representative of the flux of the said radiation in the integrating enclosure when no diamond is in the integrating enclosure;
   means for combining said third and fourth signals to give a signal dependent upon the total surface area of the diamond; and
   means for comparing the signal dependent upon the surface area of the region of the diamond that strongly absorbs radiation substantially of wavelength substantially in the range 230 nm to 320 nm with the signal dependent upon the total surface area of the diamond, to thereby deduce the presence of a layer of synthetic diamond if the first-mentioned area is different to the total surface area.

4. The apparatus of claim 3, wherein the means for sensing the flux of radiation substantially of wavelength substantially in the range 230 nm to 320 nm in the integrating enclosure and giving a first signal representative of the flux of radiation substantially of wavelength substantially in the range 230 nm to 320 nm in the integrating enclosure when the diamond is in the integrating enclosure, and the means for sensing the flux of radiation of wavelength less than about 230 nm in the integrating enclosure and giving a third signal representative of the flux of radiation of wavelength less than about 230 nm in the integrating enclosure when the diamond is in the integrating enclosure, comprises:

detector means for giving a signal representative of the intensity of radiation incident upon it.

5. The apparatus of claim 3 or 4, comprising:

an alterable filter means for selectively transmitting to the detector means radiation substantially of wavelength substantially in the range 230 nm to 320 nm or of wavelength less than about 230 nm.

\* \* \* \* \*